United States Patent [19]
Kuraishi et al.

[11] Patent Number: 5,968,568
[45] Date of Patent: Oct. 19, 1999

[54] ENZYME PREPARATION FOR USE IN THE BINDING OF FOOD MATERIALS AND PROCESS FOR PRODUCING BOUND FOOD

[75] Inventors: Chiya Kuraishi; Takahiko Soeda, both of Kawasaki, Japan

[73] Assignee: Ajinomoto Co., Inc., Tokyo, Japan

[21] Appl. No.: 08/886,207

[22] Filed: Jul. 1, 1997

[30]    Foreign Application Priority Data

Jul. 1, 1996 [JP] Japan .................................. 8-171155
May 26, 1997 [JP] Japan .................................. 9-134825

[51] Int. Cl.⁶ .............................. A23L 1/31; A23L 1/05; A23L 1/311; A23L 1/0562
[52] U.S. Cl. ............................. 426/56; 426/42; 426/92; 426/302; 426/574; 426/576; 426/652; 426/657; 435/193; 530/356
[58] Field of Search .................. 426/42, 56, 92, 426/302, 657, 652, 574, 576; 435/193; 530/356

[56]    References Cited

U.S. PATENT DOCUMENTS

| | | | |
|---|---|---|---|
| 4,917,904 | 4/1990 | Wakameda et al. | 426/7 |
| 5,055,310 | 10/1991 | Nonaka et al. | 426/46 |
| 5,156,956 | 10/1992 | Motiki et al. | 435/68.1 |
| 5,518,742 | 5/1996 | Soeda et al. | 426/63 |
| 5,658,605 | 8/1997 | Soeda et al. | 426/7 |
| 5,681,598 | 10/1997 | Kuraishi et al. | 426/36 |
| 5,834,232 | 11/1998 | Bishop et al. | 435/68.1 |

*Primary Examiner*—Keith D. Hendricks
*Attorney, Agent, or Firm*—Oblon, Spivak McClelland, Maier & Neustadt, P.C.

[57]    ABSTRACT

An composition containing transglutaminase and collagen. The composition can be used to prepare bound food, preferably without the use of allergy-causing casein proteins.

13 Claims, 1 Drawing Sheet

ENZYME PREPARATION FOR USE IN THE BINDING OF FOOD MATERIALS AND PROCESS FOR PRODUCING BOUND FOOD

BACKGROUND OF THE INVENTION

1. Field of the Invention

The present invention relates to an enzyme composition useful for binding food materials, and a process for producing bound food.

2. Discussion of the Background

A variety of methods have been used to bind food materials. One method which is widely used provides a frozen or heat-treated product in many cases. However, the binding strength of the glue used in many of the known processes has not necessarily been satisfactory, and it has been difficult to bind many materials with these glues.

In order to solve this problem, Japanese Laid-Open (Kokai) No. 284,867/1994 discloses a method in which food materials are bound by using a combination of a transglutaminase (hereinafter referred to as "TGase"), which is an enzyme, and caseins (including casein as well as caseinates such as sodium caseinate and calcium caseinate, and a casein partial hydrolyzate).

This method takes advantage of crosslinks between proteins produced by the TGase. In this method, caseins are used as a binder in combination with proteins present in food materials per se to enhance the binding strength. According to this method, a raw bound food, for example, raw restructured steak meat, can be produced without being frozen or heat-treated. In recent years, this method has been widely employed, not only in Japan, but also abroad as a method of producing bound food having a high commercial value.

A technique of producing low-calorie and low-salt bound food by adding TGase and caseins, such as a casein partial hydrolyzate, to animal meat and fish meat has also been investigated.

Methods of binding food materials without using TGase have been reported, and some of them have been put to practical use. For example, a method in which pieces of meat are bound using a combination of (1) a heat-coagulable protein, such as a wheat protein or the like and (2) an alkaline earth metal salt which produces an alkaline solution in water, such as calcium oxide, calcium hydroxide or the like, is disclosed in Japanese Laid-Open (Kokai) No. 268,665/1990. However, the bound food obtained by this method has a bitter taste and an undesirable proteinaceous smell. Accordingly, this method is not acceptable.

Further, it is well-known that myosin is eluted with sodium chloride and pieces of meat can be bound using gel-formability of the eluted myosin. However, since this method requires quite a large amount of sodium chloride, the food has a strong, salty taste. In addition, the salt content is high, which is undesirable for health reasons. Further, heating is required for binding the food. Accordingly, this method can only be used with certain types of food.

For the above-mentioned reasons, a method of binding food materials through the protein crosslinking reaction with TGase is preferable, Above all, the method disclosed in Japanese Laid-open (Kokai) No. 284,867/1994 is considered to be the best technique since bound food which is excellent in taste and flavor is produced.

It is also possible to produce bound food with TGase alone without using caseins, see Japanese $2^{nd}$ publication (Koukoku) No. 55,116/1994. However, the use of TGase alone exhibits a binding strength which is inferior as compared to the combined use of TGase and caseins. Therefore, TGase and caseins provide the best results when they are used in combination. Consequently, caseins are considered in the art to be an essential component of an additive for producing bound food.

However, milk proteins cannot be used, in some cases, for producing processed food because of problems such as food allergies and the like. Especially, among milk proteins, caseins are known to cause food allergies. Further, in some foreign countries, the use of ingredients other than proteins derived from the food materials to be bound is legally controlled in accordance with the form of bound food. For example, in the Netherlands when producing processed beef steak meat, proteins derived from cattle meat, cattle bones or cattle skins can be used as a binder, but caseins derived from milk cannot.

Under such circumstances, a technique in which caseins are not used has been also studied. For example, WO 95/08274 discloses a method in which raw meat is bound by using a combination of TGase with an alkali metal phosphate and sodium chloride as a binder. However, in this method, it is indispensable to use, based on the weight of meat, 0.4% (weight %) or less of an alkali metal phosphate and as high as from 1.5 to 4% (weight %) of sodium chloride. Thus, a food product that loses the taste and flavor inherent in meat is produced.

Under these circumstances, a composition for binding food materials by which food materials such as pieces of meat or the like can be bound even in an unheated raw state without using caseins and a process for producing bound food having excellent taste and flavor have been in demand in the field of processed food.

SUMMARY OF THE INVENTION

The present inventors have assiduously conducted investigations to solve the above-mentioned problems, and have consequently found that food materials can be bound effectively using TGase and collagen, preferably without the use of caseins. This finding has led to the completion of the present invention.

That is, the present invention relates to 1) an enzyme preparation for use in binding food materials which contains TGase and collagen as active ingredients, and 2) a process for producing bound food by treating food materials with transglutaminase and collagen.

A more complete appreciation of the invention and many of the attendant advantages thereof will be readily obtained as the same becomes better understood by reference to the drawings and following detailed description.

DETAILED DESCRIPTION OF THE INVENTION

Figure 1:
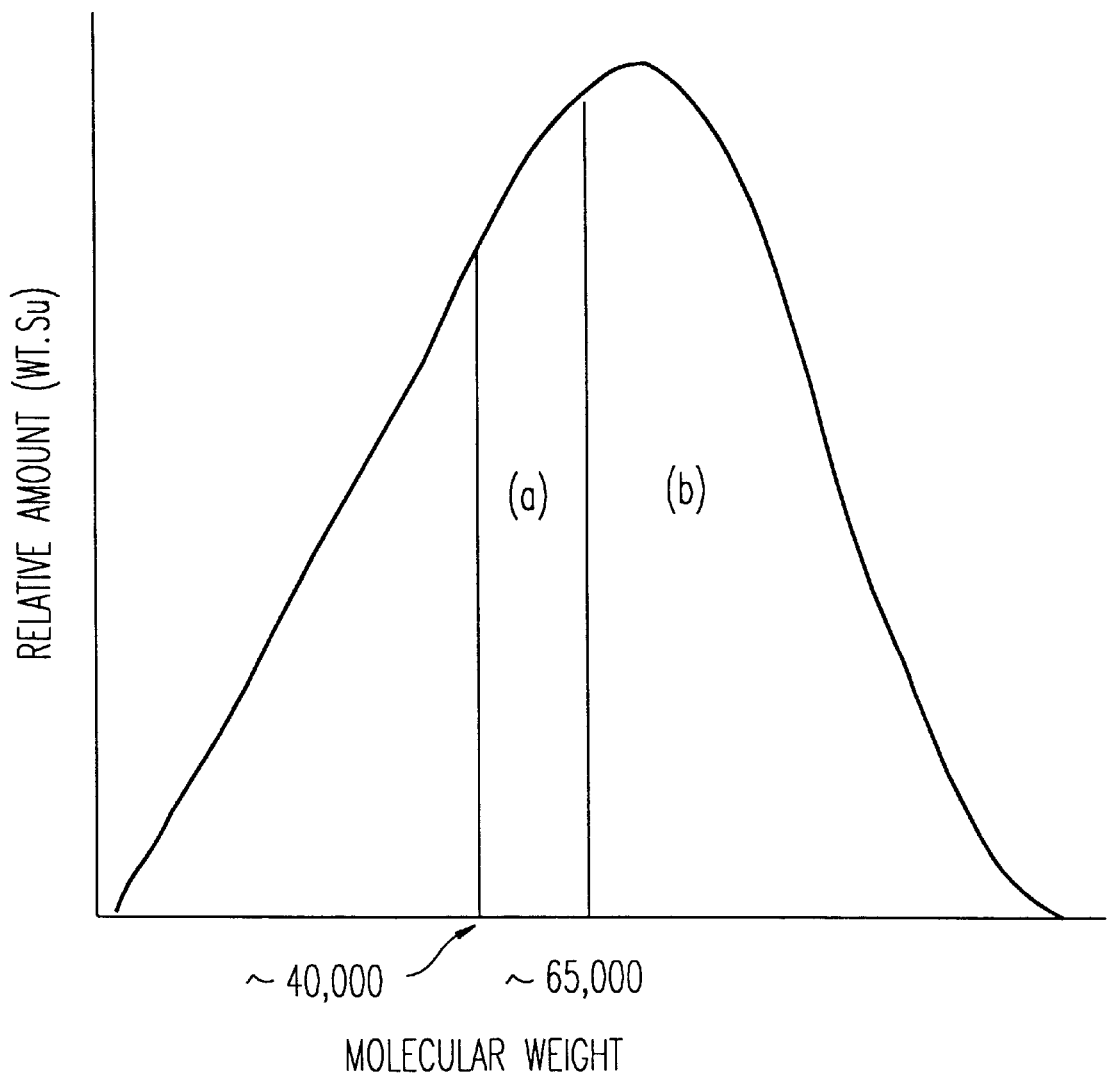
FIG. 1 shows a representative distribution of the molecular weight of the total protein in the collagen used in a preferred embodiment of the present invention. The x-axis represents the molecular weight of the protein in the collagen. The y-axis represents the relative amount (wt. %) of protein in the collagen having a given molecular weight value. The total area under the curve represents 100% by weight of the protein in the collagen. The sum of areas (a) and (b) represents at least 70% by weight of the total protein in the collagen, and corresponds to the protein having a molecular weight of greater than about 40,000. The area (b) represents at least 50% by weight of the total protein in the collagen, and corresponds to the protein having a molecular weight of greater than about 65,000.

The present composition for binding food contains TGase and collagen as active ingredients. Preferably, caseins are excluded from the composition. However, the composition may contain caseins in very small amounts, for example amounts which do not cause food allergy. Thus, the collagen can be used as the binder instead of caseins, which have been considered in the art to be indispensable for obtaining satisfactory binding strengths in the bound food. With the present composition, food materials may be bound without being heated, and the taste and flavor of the resulting bound food are excellent.

By excluding caseins from the present composition bound, food can be prepared without violating regulations which prohibit using these materials in processed food products. In addition, consumers who are allergic to these proteins can enjoy the bound food prepared according to the present invention without the fear of having an allergic reaction.

TGase is an enzyme which catalyzes the acyl transfer reaction between the γ-carboxyamide group of peptide- or protein-bound glutaminyl residues and primary amines, and which forms an ∈-(γ-Glu)Lys crosslink when the primary amine is a lysyl residue of a protein.

So long as the TGase used in the present invention has enzymatic activity, its origin is not particularly limited. Examples of TGase include TGase derived from microorganisms such as the genus Streptoverticillium and the like [hereinafter abbreviated as "BTGase"; see Japanese Laid-Open (Kokai) No. 27,471/1989 and U.S. Pat. No. 5,156,956), TGase derived from mammals, such as a guinea pig [see Japanese Laid-Open (Kokai) No. 14,964/1983], TGase derived from fish, such as a cod or the like [see Seki Nobuo et al., Nippon Suisan Gakkaishi, vol. 56, No. 1, p. 125 (1990)], TGase present in blood (called also Factor XIII), and TGase produced through the gene recombination [see, for example, Japanese Laid-Open (Kokai) Nos. 300,889/1989, 199,883/1993 and 225,775/1994, and WO 93/15234]. All of the references cited above are incorporated herein by reference. While all of the above-mentioned examples of TGase may be used in the present invention, TGase derived from microorganisms is preferred since it can be mass-produced industrially with low cost.

The amount of TGase in the present invention is not particularly limited. It is usually between 0.01 U and 100 U, preferably between 0.1 U and 50 U per gram of a food raw material to be bound. The optimum amount of TGase varies depending on the type, size and form of the food material and the form of the final product. The appropriate amount of TGase can be determined by simple experiments based on the abovementioned ranges.

The activity unit of TGase referred to in the present invention may be measured and defined by the following hydroxamate method. That is, TGase functions in a reaction system containing benzyloxycarbonyl-L-glutamylglycine and hydroxylamine as substrates in a Tris buffer of pH 6.0 at a temperature of 37° C., and the hydroxamic acid formed is converted into a ferric complex in the presence of trichloroacetic acid. Then, an absorbance at 525 nm of the reaction system is measured, and the amount of hydroxamic acid formed is calculated using a standard calibration curve. The amount of the enzyme that catalyzes formation of 1 μmol of hydroxamic acid in 1 minute is defined as an activity unit of TGase, namely 1 unit (1 U). For a description of this method, see Japanese Laid-Open (Kokai) No. 27,471/1989 and U.S. Pat. No. 5,156,956, both incorporated herein by reference.

Collagen is the other important ingredient required in the present invention. Any type of collagen may be used.

Preferably, the collagen used in the present invention is an extraction product of animal bone and/or an animal skin. Also, at least 70% by weight of the total protein in the collagen has a molecular weight of greater than approximately 40,000 and at least 50% by weight of the total protein in the collagen has a molecular weight of greater than approximately 65,000 (see FIG. 1). The use of the collagen having the abovementioned molecular weights remarkably increases the binding effect.

As is understandable from the above-mentioned molecular weights, collagen referred to in the present invention also includes gelatin which is formed through decomposition or modification of collagen. For a description of collagen and gelatin, see Kirk-Othmer Encyclopedia of Chemical Technology, Third Edition, volume 11, 1980, pp. 711–719, incorporated herein by reference.

The origin of collagen is not particularly limited, and generally a bone or a skin of an animal such as cattle, pig, poultry, sheep, goat or the like can be used. Further, the collagen may not be a purified product, and collagen containing fats, carbohydrates, peptides, amino acids and the like may also be used.

Collagen is preferably extracted from animal bone and/or animal skin and purified. During extraction and purification, collagen is hydrolyzed to various extent. Accordingly, it may have wide-ranging molecular weight distribution.

In order to obtain the collagen having the abovementioned preferred molecular weights, the molecular weights may be measured in the following manner.

A method of fractionating a protein according to molecular weights through molecular sieves, for example, gel filtration or SDS-PAGE (SDS-polyacrylamide gel electrophoresis) can be employed. The molecular weights of the fractions can be estimated using a commercial molecular weight marker. The measured molecular weights are weight-average molecular weights.

Of course, the definition of the effective molecular weights may vary somewhat depending on the measuring method. Further, the molecular weights measured usually involve an error of approximately up to 5%. Collagen having the above-mentioned molecular weights, even though it is measured by any measuring method, exhibits the sufficient binding effect. In the present invention, the molecular weights of collagen were measured through SDS-PAGE to clarify the relation between the molecular weights and the binding strength.

Consequently, when using collagen composed mainly of a fraction having a low molecular weight, the binding effect is decreased This is presumably because the reactivity with TGase is reduced owing to the low molecular weight.

For example, a hydrolyzate of an animal protein (tradename: CEBAPRO C) in which more than 90% (weight %) of the overall material is composed of a peptide or an amino acid having a molecular weight of 5,000 or less is approximately the same as a collagen (trade name: "SCAN-PRO T 95") which is effective in the present invention in terms of amino acids composition, but the molecular weight is too low. Accordingly, the binding effect is extremely low.

Collagen in the reaction system may be used in any amount where it serves as a substrate of an enzyme (e.g., the TGase) and as a binder. This amount is usually between 0.1 and 5 parts by weight, preferably between 0.5 and 2 parts by weight per 100 parts by weight of the food materials to be bound.

When the amount of collagen is too small the binding effect when using collagen and TGase together is the same as that when using TGase alone. When the amount of collagen is too large, a thick protein membrane is formed between the food materials. This is undesirable in view of the eating feel and the binding strength. Of course, the above-mentioned ranges represent the preferred embodiments. More or less than these amounts may be used, if desired.

The proportions of TGase and collagen which are essential ingredients of the enzyme preparation for use in the binding of food materials in the present invention are not particularly limited. The proportion of collagen is usually between 20 and 80 parts by weight per 100 parts by weight of the enzyme preparation. The proportion of TGase is usually between 1 and 200 U, preferably between 10 and 150 U per gram of the enzyme composition.

In the enzyme preparation of the present invention, TGase and collagen are not necessarily blended and packed in one container. They may be packed in different containers in the form of a kit.

The enzyme composition and the kit of the present invention contain TGase and collagen as essential active ingredients. They may also contain the following additional additives.

For example, the composition may contain a food excipient. Examples thereof include lactose, sucrose, maltit, sorbitol, dextrin, branched dextrin, cyclodextrin, starches, polysaccharide, gums and pectin.

Further, the enzyme preparation of the present invention or the kit may also contain proteins. As discussed above, caseins are preferably excluded. Examples thereof include a protein (a mixture of gelatin, myosin and the like) extracted with water from meat such as pork, beef, mutton or fowl, a protein obtained by forming the above-mentioned meat into a paste using a chopper, a soybean protein, a wheat protein and so forth. In view of the allergies which may be caused by the bound food, however, it is advisable to refrain from incorporating the strongly antigenic soybean protein and wheat protein into the enzyme preparation, as much as possible.

Further, the enzyme preparation or the kit of the present invention may contain salts such as sodium bicarbonate, sodium citrate, sodium phosphate, sodium chloride and potassium chloride and so on.

Still further, the enzyme preparation or kit may contain a seasoning, sugar, a flavoring agent, a coloring agent, a color fixative, ascorbic acid and its salt, an emulsifying agent, fats and oils and so on.

As stated above, the enzyme preparation of the present invention is characterized in that 1) TGase and collagen are used as essential ingredients and 2) caseins which have been deemed essential to provide the practical binding strength but which cause the allergy problem are preferably excluded.

There are at least two processes for producing bound food by binding food materials: (1) a process in which an enzyme preparation comprising TGase and collagen as active ingredients is used as such, and (2) a process in which TGase and collagen are used separately. Both of these processes are effective in the present invention.

In both of these processes, the amount of TGase relative to the food materials and the amount of collagen relative to the food materials may be the same. That is, the amount of TGase is usually between 0.01 U and 100 U, preferably between 0.1 U and 50 U per gram of the food materials to be bound. Further, the amount of collagen is usually between 0.1 and 5 parts by weight, preferably between 0.5 and 2 parts by weight per 100 parts by weight of the food materials. Accordingly, whether TGase and collagen are used in the form of the enzyme preparation or separately from each other, they are preferably used in the above-mentioned amounts.

In the present invention, it is preferable that a glue obtained by adding collagen to cold water having a temperature of 10° C. or less, preferably to cold water having a temperature of 5° C. or less be used as a binder. The cold water may contain ice in order to maintain the desired temperature.

The reason for adding collagen to cold water at 10° C. or less is that the collagen, especially collagen having the above-mentioned predetermined molecular weights, is well dispersed in cold water having a temperature of 10° C. or less, and after dispersed, forms a glue which is easily miscible with food materials. Since this glue adheres to the surface of the food material uniformly, it serves extremely well as a binder to enhance the binding with the food material by the TGase. This is believed to give the final product its high binding strength.

When collagen is added to water having a temperature above 10° C., the dispersion state becomes poor (so-called "clumps" maybe formed), and it can hardly be mixed with the food materials.

In the present invention, it is also preferable that the weight ratio of cold water to collagen is adjusted to from 6:1 and 20:1, preferably between 10:1 and 14:1. The reason is that this ratio contributes to remarkably improved binding strength.

When the ratio of cold water to collagen exceeds 20, the viscosity is lowered owing to the high content of cold water. Meanwhile, when the ratio is less than 6, the viscosity is increased owing to the low content of cold water. In either case, a glue that exhibits a desirable viscosity for producing bound foods may not be obtained.

A process for producing bound food in accordance with the present invention is described below.

A predetermined amount of collagen is added to cold water at 10° C. or less to form a glue. Subsequently, this glue is mixed with food materials and TGase. Since this glue serves as a binder between the food materials, the food materials are bound quite strongly through the enzymatic function of the TGase. The order of mixing the food materials and TGase with the obtained glue is not particularly limited. The glue may be first mixed with the food materials and then with TGase, or vice versa. Further, the food materials and TGase may be mixed with the glue at the same time.

Still further, it is also possible that TGase and collagen are added to cold water at 10° C. or less to form a glue, and this glue is then mixed with the food materials.

The TGase and collagen may be used separately. Alternatively, the enzyme composition of the present invention which contains TGase and collagen mixed together as essential ingredients may be used.

In addition to TGase and collagen as essential ingredients, the above-mentioned additives such as seasonings, sodium chloride, spices, sugars, emulsifying agents, sodium bicarbonate, excipients and the like may be added as desired.

When a product is not necessarily limited to a low salt content, sodium chloride may be added to the glue obtained by adding collagen to cold water at 10° C. or less, so that the binding strength is markedly improved.

The mixture of the glue and the food materials is preferably directed to a forming process immediately.

In the forming process, the mixture is filled in a ordinary forming container such as a casing tube or the like, and allowed to stand at from 0 to 65° C. for from 5 minutes to 24 hours. During that time, TGase acts to produce the desired bound-formed food. The resulting bound-formed food may be heated or frozen as required.

Bound food may be produced by directly coating uniformly (1) an enzyme preparation containing TGase and collagen as essential ingredients or (2) TGase and collagen separately on surfaces of food materials, though this bound food is slightly inferior in the binding effect compared with the bound food produced by the foregoing process in which the glue obtained by adding collagen to cold water at 10° C. or less is used as a binder.

Finally, the food materials used in the present invention are described below.

The food materials are preferably any proteinaceous foods. Examples thereof include animal meat, such as beef, pork, horsemeat, mutton, goat, rabbit meat and chicken; fish meat; shells; shellfishes, such as a shrimp and crab; mollusk, such as a cuttlefish and octopus; and fish eggs, such as salmon roe. Further, processed food such as cheese, noodles or a boiled fish paste may also be used.

The present invention can be applied to all of the above-mentioned proteinaceous food materials. When the present invention is used to bind animal meat (such as beef, pork, horsemeat, mutton, goat, rabbit meat and fowl), the binding effect is most pronounced.

When the binding of meat is conducted in accordance with the present invention, the binding strength of the practical level may be obtained without using proteins which are likely to cause allergy, such as caseins. Further, the product obtained by the present invention is a processed meat product containing only meat-derived materials, except for the TGase.

EXAMPLES

Having generally described this invention, a further understanding can be obtained by reference to certain specific examples which are provided herein for purposes of illustration only and are not intended to be limiting unless otherwise specified.

Example 1

Production of an Enzyme Composition for use in Binding Food Materials

Two types of enzyme preparations in the present invention were produced according to recipe (a) or (b) as shown in Table 1. A commercial transglutaminase (Available from Ajinomoto Co., Inc., specific activity 1 U/mg) of the genus Streptoverticillium mobaraense IFO 13819) was used. Further, as collagen, "SCANPRO T 95" (obtained from Protein Foods A/S, Denmark) was used.

"SCANPRO T95" is a material prepared from a pig skin in a usual manner. Analysis of this material by SDS-PAGE revealed that the amount of the protein having a molecular weight of 65,000 or more was 67.7% by weight of the total protein and the amount of the protein having a molecular weight of 40,000 or more was 75.6% by weight of the total protein.

TABLE 1

| Enzyme Preparation | Recipe | |
|---|---|---|
| (a) | collagen | 70 g |
| | branched dextrin | 30 g |
| | TGase | 6,000 U |
| (b) | collagen | 60 g |
| | lactose | 40 g |
| | TGase | 10,000 U |

Example 2

Production of Bound Pork Using the Enzyme Preparation

Ten grams of the enzyme preparation of the present invention which was produced in Example 1 were added to, and dispersed in, cold water (3° C.) of an amount (weight) which was 7 times as large as that of the enzyme preparation, to obtain a glue. This glue was then used as a binder. That is, this glue was uniformnly mixed well with a total of 1 kg of small pieces (approximately 2-cm cubes) of ham, Then, the mixture was filled in a casing tube having a folding width of 75 mm, and allowed to stand at 20° C. for 1 hour to produce bound raw pork. The processed pork filled in the casing tube was frozen as such in a freezer at −25° C. until the being strength evaluation was conducted The product formed in the above-mentioned manner, except that the enzyme preparation of the present invention was not added, was used as a control.

The frozen bound pork was sliced to a thickness of 9 mm. After this, the pork was thawed, the binding strength of the raw pork was measured. Both surfaces thereof were baked on a hot plate, and an organoleptic evaluation was conducted.

The binding strengths of the raw bound pork products obtained by using the enzyme preparations (a) and (b) were more than 60 g/cm$^2$ in terms of the binding strengths. Thus, they had a binding strength as required for bound pork products. Meanwhile, in the control product, the small pieces of meat were not bound at all to one another.

During grilling, the product of the present invention did not cause delamination of bound surfaces, and the product had a natural eating feel. Its excellent taste and flavor were the same as those of a product obtained by grilling natural, fresh pork.

Since the collagen used was derived from pork, the bound pork obtained by using this collagen was a processed meat food containing only pork-derived ingredients, except for a trace amount of TGase.

Example 3

Influence of the Ratio of Water to Collagen on the Binding Strength

With respect to the enzyme preparation (a) in Table 1, the influence of a ratio of cold water to collagen on the binding was examined. The binding experiment was conducted in the same manner as in Example 2. The results are shown in Table 2.

TABLE 2

| Ratio of cold water (3° C.) to collagen | binding strength (g/cm²) |
| --- | --- |
| 4 | 25 |
| 6 | 50 |
| 8 | 61 |
| 10 | 73 |
| 12 | 78 |
| 14 | 76 |
| 16 | 66 |
| 18 | 64 |
| 20 | 58 |
| 22 | 45 |

As is clear from Table 2, binding strength varied greatly by changing the ratio of cold water (3° C.) to collagen.

That is, when cold water was added at a ratio of from 6 to 20 parts by weight per 1 part by weight of collagen, the binding strength was as high as 50 g/cm² or more. This was presumably because collagen added to the cold water was dispersed therein quite well (the clumps were hardly formed) to form an excellent "glue" which gave rise to the high binding strength.

Example 4

Production of Bound Pork

Ten grams of collagen (tradename: "SCANPRO T 95") described in Example 1 were added to 110 g of cold water (3° C.), and these were mixed well immediately to form a glue. Subsequently, this glue was used as a binder. That is, a total of 1,000 g of small pieces (approximately 2-cm cubes) of ham were charged into this glue, and they were mixed well with each other.

To this was added a mixture obtained by previously dissolving 1,000 U of TGase (powder) into a small amount (5 ml) of water. The small pieces of meat, TGase and the collagen glue were uniformly mixed well (the amount of TGase was 1 U per gram of meat and that of collagen was 0.01 g on the same basis).

Subsequently, this mixture was packed into a casing tube having a folding width of 75 mm, and allowed to stand at 5° C. for 4 hours to proceed with the TGase reaction. Then, the reaction mixture was placed in a freezer at −40° C., and frozen until the evaluation was conducted. As a control, bound pork was prepared by using collagen alone without adding TGase.

The frozen bound pork was sliced to a thickness of 9 mm. After this, the pork was thawed and the binding strength of the raw bound pork was measured using a rheometer. Both surfaces thereof were baked on a hot plate, and an organoleptic evaluation was conducted.

The binding strength of the raw bound pork of the present invention was 51 g/cm², and that of the control was 10 g/cm² in terms of the binding strength. The value of 10 g/cm² for the control was so low that the bound pork could barely be lifted up, and it was far from the binding required for practical use. On the other hand, the bound pork product of the present invention could be satisfactorily handled.

The product of the present invention did not cause delamination of bound surfaces during the grilling, and the eating feel was natural. The taste and flavor thereof were the same as those of a product obtained by grilling natural, fresh meat.

Example 5

Production of Bound Pork Containing Sodium Chloride

Ten grams of collagen (tradename: "SCANPRO T 95") and 1,000 U of TGase were added to 100 g of cold water (5° C.) to form a glue. This glue was mixed with 10 g of sodium chloride. Subsequently, this glue was uniformly mixed well with 1,000 g of small pieces of ham (approximately 2-cm cubes). The resulting mixture was packed into a casing tube having a diameter of 4.5 cm, and allowed to stand at 5° C. for 4 hours to proceed with the enzymatic reaction. Subsequently, the reaction product was placed in a freezer at −40° C., and frozen until the evaluation was conducted.

The frozen bound pork was sliced to a thickness of 9 rm. After the pork was thawed, the binding strength of the raw bound port was measured using a rheometer.

When sodium chloride was added, the binding strength of the raw bound pork which was bound by the process of the present invention was 80 g/cm².

The binding strength of the resulting bound food was at least approximately 1.5 times as high as the bound food prepared in exactly the same manner except that no sodium chloride was added. This demonstrates that the binding strength of the food materials was further increased with the use of sodium chloride.

When sodium chloride is added to the glue so that the binding effect may be enhanced, a procedure such as tumbling or the like is not required. Accordingly, sodium chloride can be used with or without a tumbling process.

Example 6

Production of Processed Chicken Tender Meat Fillet

Ten grams of collagen (tradename: "SCANPRO T 95") were added to 100 g of cold water at 3° C., and mixed well. When collagen became a glue, 500 U of TGase (powder) were charged therein, and the components were mixed.

This glue was mixed with 1,000 g of small pieces of chicken tender meat such that they were uniformly entangled with each other (an amount of TGase was 0.5 U per gram of meat, and that of collagen was 0.01 g on the same basis).

Subsequently, this mixture was put on a retainer, and allowed to stand at 5° C. for 2 hours to proceed with the TGase reaction. Then, the reaction product was placed in a freezer at −40° C., and frozen until the evaluation was conducted. As a control, chicken tender meat which was bound in the above-mentioned manner using collagen alone without adding TGase was used.

The frozen bound tender meat fillet was sliced to a thickness of 10 mm. After it was thawed, the binding strength of this fillet in the raw state was measured using a rheometer.

When the binding strength of the samples was measured, the control product was not bound at all, hence the binding strength was unmeasurable. Meanwhile, the product of the present invention had the binding strength of 52 g/cm², and it was, therefore, completely processed in the form of a piece of chicken fillet.

Chicken tender meat usually has a low binding strength because it is hard to use chicken tender meat as the starting material for processed food because only small pieces of meat are obtained. However, according to the present invention, it was possible to obtain fillet which could be processed into a larger chicken steak meat. This experimental result revealed the possibility of improving the commercial value of chicken tender meat with the present invention.

Example 7

Production of a Fried Pork Cutlet by a Powder Coating Method

Seventy grams of collagen (tradename: "SCANPRO T 95"), 30 g of branched dextrin and 6,000 U of TGase were mixed to produce an enzyme preparation for bound food.

This enzyme preparation was placed on a tray at a fixed thickness. Small pieces (approximately 2-cm cubes) of pork loin were placed on this tray, and the surfaces of the small pieces of pork loin were uniformly coated with the enzyme preparation by rolling. The thus-treated small pieces of pork loin were put into a retainer for fried pork cutlet, allowed to stand at room temperature for 2 hours to conduct the enzymatic reaction of TGase, and then frozen overnight in a freezer at −40° C. The amounts of TGase and collagen adhered to the small pieces of meat were 0.5 U and 0.01 g per gram of meat respectively.

A preparation comprising 70 g of collagen and 30 g of branched dextrin was produced as a control, and coated on small pieces of pork loin. The thus-coated small pieces of pork loin were treated in the same manner as in the product of the present invention to give a fried pork cutlet.

The frozen bound pork was sliced to a thickness of 9 mm. After it was thawed, batter and bread crumbs were coated thereon, and the thus-treated pork was fried in oil at 175° C. for 5 minutes to obtain a fried pork cutlet.

The invention product and the control product were compared with respect to the battering and crumbing. The organoleptic evaluation of the fried pork cutlet was also conducted.

In the bound pork which was produced using the enzyme preparation of the present invention, the small pieces of meat were not separated from one another even during battering and crumbing, and the obtained fried pork cutlet was identical to that obtained by using one large piece of pork loin.

On the other hand, in the control product, the small pieces of meat, at a glance, seemed to be bound immediately after the slicing. However, when this product was dipped in a batter solution and bread crumbs were pressed thereon, the small pieces of meat were separated from one another. It was completely impossible to obtain a bound fried pork cutlet just like one large piece of pork loin.

In the results of the organoleptic evaluation, when the invention product was eaten, the satisfactory meat fibrous feeling was observed, and no unpleasant feelings were reported.

Obviously, numerous modifications and variations of the present invention are possible in light of the above teachings. It is therefore to be understood that within the scope of the appended claims, the invention may be practiced otherwise than as specifically described herein.

This Application is based on Japanese Application No. 171155/1996, filed Jul. 1, 1996, and No. 134825/1997, filed May 26, 1997. Both of these Applications are incorporated herein by reference in their entirety.

What is claimed as new and desired to be secured by Letters Patent of the United States:

1. A composition, comprising a transglutaminase a collagen and water, wherein
   the collagen is an extraction product of animal bone and/or animal skin;
   at least 70% by weight of the total amount of protein in the collagen has a molecular weight of greater than approximately 40,000; and
   at least 50% by weight of the total protein in the collagen has a molecular weight of greater than approximately 65,000, and wherein the composition is obtained by either (1) combining said transglutaminase and said collagen in said water at a water temperature of at most 10° C., or (2) combining said collagen in said water at a water temperature of at most 10° C., and then adding said transglutaminase, wherein the ratio of water to collagen in said composition is from 4 to 22 parts by weight per 1 part by weight of collagen.

2. The composition of claim 1, comprising from 1 to 200 U of the transglutaminase per gram of the composition, and from 20 to 80 parts by weight of the collagen per 100 parts by weight of the composition.

3. The composition of claim 1, further comprising at least one food.

4. The composition of claim 3, comprising from 0.01 to 100 U of the transglutaminase per gram of the composition, and from 0.1 to 5 parts by weight of the collagen per 100 parts by weight of the composition.

5. The composition of claim 1, wherein the weight ratio of the water to the collagen is from 6:1 to 20:1.

6. A process for preparing bound food, comprising applying a composition comprising a transglutaminase, a collagen and water to at least one food, wherein
   the collagen is an extraction product of animal bone and/or animal skin;
   at least 70% by weight of the total amount of protein in the collagen has a molecular weight of greater than approximately 40,000; and
   at least 50% by weight of the total protein in the collagen has a molecular weight of greater than approximately 65,000, and wherein the composition is obtained by either (1) combining said transglutaminase and said collagen in said water at a water temperature of at most 10° C., or (2) combining said collagen in said water at a water temperature of at most 10° C., and then adding said transglutaminase, wherein the ratio of water to collagen in said composition is from 4 to 22 parts by weight per 1 part by weight of collagen.

7. The process of claim 6, wherein the surface of the food is coated with the composition.

8. The process of claim 6, wherein the water has a temperature of at most 5° C.

9. The process of claim 6, wherein the weight ratio of the water to the collagen is from 6:1 to 20:1.

10. The process of claim 6, wherein the weight ratio of the water to the collagen is from 8:1 to 18:1.

11. The process of claim 6, comprising combining the collagen and the water to produce a glue, followed by combining the glue with the transglutaminase and the food.

12. The process of claim 6, comprising combining the collagen, the transglutaminase and the water to produce a glue, followed by combining the glue with the food.

13. The process of claim 6, wherein the water contains sodium chloride.

* * * * *